(12) United States Patent
Hasebe

(10) Patent No.: US 7,895,888 B2
(45) Date of Patent: *Mar. 1, 2011

(54) THERMAL MASS FLOW METER INCLUDING HEATING ELEMENT AND TEMPERATURE SENSORS FORMED ON SEPARATE CHIPS AND SECURED TO THE OUTER PERIPHERY OF THE PIPE

(75) Inventor: Shinya Hasebe, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 230 days.

This patent is subject to a terminal disclaimer.

(21) Appl. No.: 12/294,908

(22) PCT Filed: Mar. 28, 2006

(86) PCT No.: PCT/JP2006/306310

§ 371 (c)(1),
(2), (4) Date: Sep. 26, 2008

(87) PCT Pub. No.: WO2007/110934

PCT Pub. Date: Oct. 4, 2007

(65) Prior Publication Data

US 2010/0162810 A1    Jul. 1, 2010

(51) Int. Cl.
*G01F 1/68* (2006.01)
(52) U.S. Cl. .................................. 73/204.27
(58) Field of Classification Search ........... None
See application file for complete search history.

(56) References Cited

U.S. PATENT DOCUMENTS

| | | | | |
|---|---|---|---|---|
| 4,519,246 A | * | 5/1985 | Hartemink | ............ 73/202.5 |
| 4,829,814 A | * | 5/1989 | Suzuki et al. | ............ 73/114.34 |
| 5,741,968 A | | 4/1998 | Arai | |
| 6,062,077 A | * | 5/2000 | Azima | ............ 73/204.27 |
| 6,208,254 B1 | * | 3/2001 | McQueen et al. | ............ 340/603 |
| 6,318,171 B1 | * | 11/2001 | Suzuki | ............ 73/204.27 |

(Continued)

FOREIGN PATENT DOCUMENTS

JP     2000-304584 A     11/2000

(Continued)

OTHER PUBLICATIONS

International Search Report for the Application No. PCT/JP2006/306310 mailed May 2, 2006.

(Continued)

*Primary Examiner*—Harshad Patel
(74) *Attorney, Agent, or Firm*—Cheng Law Group, PLLC

(57) ABSTRACT

A heater chip (4) as a heat generation element is secured to the surface on the periphery of piping (2). Further, a temperature sensor chip couple (6) is placed on the surface on the periphery of the piping (2), along the direction of flow of fluid flowing in the piping (2). One (6a) of the sensor chips in the couple is placed on the upstream side of the heater chip (4) and the other (6b) is placed on the downstream side of the heater chip (4). The heater chip (4) and the temperature sensor chips (6a, 6b) are formed in a chip type. The temperature sensor chips (6a, 6b) as the pair are placed at positions spaced by the same distance from the heater chip (4).

9 Claims, 6 Drawing Sheets

U.S. PATENT DOCUMENTS

| | | | |
|---|---|---|---|
| 6,354,150 B1 * | 3/2002 | Rudent et al. | 73/202.5 |
| 6,628,202 B2 * | 9/2003 | McQueen et al. | 340/603 |
| 6,681,625 B1 * | 1/2004 | Berkcan et al. | 73/204.23 |
| 6,813,944 B2 | 11/2004 | Mayer et al. | |
| 7,028,544 B2 * | 4/2006 | Besseling et al. | 73/202.5 |
| 7,036,369 B2 * | 5/2006 | Keppner et al. | 73/204.26 |
| 7,104,112 B2 * | 9/2006 | Bonne | 73/23.25 |
| 7,181,963 B2 * | 2/2007 | Bork | 73/204.26 |
| 7,258,003 B2 * | 8/2007 | Padmanabhan et al. | 73/204.26 |
| 7,565,836 B2 * | 7/2009 | Sukegawa et al. | 73/204.27 |
| 7,600,422 B2 * | 10/2009 | Hasebe | 73/204.17 |
| 7,617,724 B2 * | 11/2009 | Hasebe | 73/204.27 |
| 2008/0148841 A1 * | 6/2008 | Sakai | 73/204.26 |

FOREIGN PATENT DOCUMENTS

| | | |
|---|---|---|
| JP | 3229168 B2 | 11/2001 |
| JP | 2003-532099 A | 10/2003 |

OTHER PUBLICATIONS

The First Office Action for the Application No. 200680053997.0 from The State Intellectual Property Office of People's Republic of China dated Mar. 29, 2010.

* cited by examiner

US 7,895,888 B2

THERMAL MASS FLOW METER INCLUDING HEATING ELEMENT AND TEMPERATURE SENSORS FORMED ON SEPARATE CHIPS AND SECURED TO THE OUTER PERIPHERY OF THE PIPE

TECHNICAL FIELD

This invention relates to a thermal mass flow meter that measures a mass flow rate of a fluid flowing through piping based upon a temperature distribution of the fluid in the flowing direction of the fluid.

BACKGROUND ART

Referring to FIGS. 7A and 7B, the following description will discuss a conventional thermal mass flow meter. FIG. 7A is a cross-sectional view that shows one example of a conventional thermal mass flow meter and FIG. 7B is a graph that shows a temperature distribution on the surface of the piping of FIG. 7A. In FIG. 7B, the axis of ordinate represents the temperature, and the axis of abscissas represents the position of the piping in a flowing direction. A curved line, indicated as a dashed line, represents the temperature distribution in a state with no fluid flowing through the piping, and a curved line, indicated by a solid line, represents the temperature distribution in a state with a fluid flowing through the piping.

As shown in FIG. 7A, a heat generating element 32 is secured on the surface of a periphery of piping 30 in contact therewith, and paired temperature sensors 34 (34a, 34b), which are used for measuring the surface temperature of the piping, are placed at positions in the flowing direction of the piping 30 on the upstream side and the downstream side of the heat generating element 32, with the same distance apart therefrom. In this example, a flow-rate measuring chip 36 in which the heat generating element 32 and paired temperature sensors 34 are assembled in a single substrate by using, for example, a MEMS (Micro Electro Mechanical System) technique, and the flow-rate measuring chip 36 is attached to the piping 30 so that the flow rate in the piping 30 can be measured (for example, see Patent Document 1).

In the thermal mass flow meter, when a fluid inside piping stands still, the fluid inside the piping is heated to a predetermined temperature by the heat generating element 32, and the surface temperatures of the piping 30 at the respective positions are measured by the paired temperature sensors 34 placed with a fixed distance apart from the heat generating element 32. On the assumption that the temperature distribution of the fluid heated by the heat generating element 30 follows Gaussian distribution, when the fluid stands still, the temperatures detected by the two temperature sensors 34a and 34b are equal to each other, with the temperature difference between the two positions being zero. As shown in FIG. 7B, when the fluid flows through the piping 30, the temperature distribution is shifted toward the downstream side so that the temperatures detected by the temperature sensors 34a and 34b have a difference. The temperature distribution of the surface of the piping 30 is shifted toward the downstream side as the flow rate of the fluid flowing through the piping 30 increases; therefore, when the apex of the temperature distribution of the surface of the piping 30 is located between the temperature sensors 34a and 34b, the difference in measured temperatures of the paired temperature sensors 34 has a greater value as the flow rate of the fluid flowing through the piping 30 increases. In this manner, since there is a correlation between the flow rate of the fluid flowing through the piping 30 and the difference in measured temperatures between the paired temperature sensors 34, the flow rate of the fluid flowing through the piping 30 can be calculated by utilizing the difference in measured temperatures between the paired temperature sensors 34 based upon the correlation.

In this thermal mass flow meter using the chip 36 for use in measuring the flow rate in which the heat generating element 32 and the paired temperature sensors 34a and 34b are assembled together with each other, the paired temperature sensors 34 can be placed near the heat generating element by using the MEMS technique; therefore, even in the case where the amount of transfer of the temperature distribution is small, since the temperature sensors 34a and 34b can measure the temperatures at positions, each having an abrupt inclination, of the curved line (see FIG. 7B) indicating the temperature distribution of the temperature sensor, it becomes possible to obtain a greater value as a measured temperature difference even in the case of a fine amount of flow rate, and consequently to carry out a flow rate measuring process with high sensitivity.

Patent Document 1: U.S. Pat. No. 6,813,944

DISCLOSURE OF THE INVENTION

Problems to be Solved by the Invention

However, the process for assembling the heat generating element 32 and the paired temperature sensors 34 onto a single substrate by using the MEMS technique requires expensive manufacturing facilities, and can not be achieved at low costs.

In order to solve this problem, the objective of the present invention is to provide a thermal mass flow meter capable of measuring a flow rate of a fluid flowing through piping at low costs.

Means to Solve the Problems

A thermal mass flow meter in accordance with the present invention is provided with: a heat generating element in a chip type for heating a fluid inside piping, which is secured onto a surface of a periphery of the piping; paired temperature sensors in a chip type that are formed as members separated from the heat generating element and secured to positions on the upstream side and the downstream side of the heat generating element on the surface of the piping, with an equal distance apart therefrom, along the flowing direction of the fluid inside the piping; and an operation unit that finds a flow rate of the fluid flowing through the piping from a temperature difference of the paired temperature sensors.

Here, in the case where a chip in which, as shown in FIG. 7A, a heat generating element 32 and paired temperature sensors 34 are assembled on a substrate closely to each other is used, since the heater and the temperature sensors are located closely, a measuring process with high sensitivity is available, within a low flow rate range of about nL/min order, for example, in the case of a high-pressure liquid chromatograph; however, within a high flow rate range of, for example, μL/min order and mL/min order, the apex of the temperature distribution of the surface of the piping is not located between the paired temperature sensors, with the result that a problem arises in which the correlation between the measured temperature difference of the paired temperature sensors and the flow rate of a fluid is no longer satisfied, failing to carry out an accurate flow rate measuring process.

Therefore, in one preferable embodiment of the thermal mass flow meter of the present invention, two pairs or more of the paired temperature sensors are preferably placed at positions having different distances from the heat generating element, and the operation unit is allowed to find the flow rate by using a temperature measuring signal from any of the pairs of the paired temperature sensors in response to the size of the flow rate. With this arrangement, the paired temperature sensors to be used for measurements can be selected in accordance with the flow rate range of a fluid flowing through the piping, thereby making it possible to widen the measurable flow rate range.

In the above-mentioned arrangement, the operation unit preferably finds the flow rate by using the pair of the paired temperature sensors in which the temperature sensor on the downstream side is located on the downstream side from an apex position of a temperature distribution of the fluid flowing through the piping, and is located closest to the apex position, among the paired temperature sensors.

Moreover, the heat generating element and temperature sensors are preferably secured to the piping through a bonding process by using a thermal conductive adhesive.

In the thermal mass flow meter of the present invention, the piping may be preferably embedded in a groove on a substrate, with a part of the surface of the periphery of the piping being exposed, and the heat generating element and temperature sensors are secured to the exposed surface. Alternatively, the heat generating element and temperature sensors may be preferably supported on a substrate and secured thereto, with the piping being anchored onto the heat generating element and temperature sensors.

In this case, the substrate is a printed circuit board on which a wiring pattern is formed, and preferably, the heat generating element and the temperature sensors are electrically connected to the wiring pattern.

In one of preferable applications of the thermal mass flow meter of the present invention, the piping to which the thermal mass flow meter is attached is prepared as piping through which a mobile phase of a high-pressure liquid chromatograph is allowed to flow.

Effects of the Invention

In the thermal mass flow meter of the present invention, not a flow-rate measuring chip in which a heat generating element and paired temperature sensors are integrally formed on a single substrate, but a heat generating element and paired temperature sensors, respectively manufactured independently, are utilized so that it becomes possible to measure the flow rate of a fluid flowing through piping at low costs, without the necessity of using an MEMS technique that is expensive in its facility investments.

Moreover, two or more pairs of the paired temperature sensors are placed on the upstream side and the downstream side of the heat generating element, and the flow rate is found by using a temperature measuring signal from any of the pairs of the paired temperature sensors in accordance with the size of the flow rate; thus, it becomes possible to measure the flow rate of fluids within a wider range.

When securing the heat generating element and the temperature sensors to the piping is carried out through bonding by using a thermal conductive adhesive, heat generated by the heat generating element can be efficiently transmitted to the piping, and the temperature of the surface of the piping can be measured by the temperature sensors accurately.

In the thermal mass flow meter of the present invention, in which the piping is preferably embedded in the groove on the substrate with a part of the surface of the periphery of the piping being exposed, and the heat generating element and temperature sensors are secured to the exposed surface, or the heat generating element and temperature sensors are supported on the substrate and secured thereto with the piping being anchored onto the heat generating element and temperature sensors; thus, it becomes possible to easily carry out attaching the heat generating element and the temperature sensors.

Moreover, in the case where the above-mentioned substrate is prepared as the printed circuit board, a drawing process of a terminal of the heat generating element and the temperature sensors having a small size can be carried out by utilizing the printed circuit board so that the circuit structures of the heat generating element and the temperature sensors can be simplified.

Best Mode for Carrying Out the Invention

FIG. 1A is a cross-sectional view that shows one embodiment of a thermal mass flow meter used for measuring a flow rate of a mobile phase flowing through piping of a high-pressure liquid chromatograph, and FIG. 1B is a graph that shows a temperature distribution of the piping of FIG. 1A. In FIG. 1B, the axis of ordinate indicates the temperature, and the axis of abscissas indicates the position of the piping 2 in the flowing direction. A curved line, represented by a dashed line, indicates a temperature distribution of the piping surface, caused by a heater in a state with no mobile phase flowing through the piping, and a curved line, represented by a solid line, indicates a temperature distribution of the piping surface, caused by the heater in a state with a mobile phase flowing through the piping.

In FIG. 1A, reference numeral 2 represents piping of a high-pressure liquid chromatograph. The mobile phase is allowed to flow through the piping 2 from the left side toward the right side in the figure. A heater chip 4 serving as a heat generating element, is anchored onto a surface of the periphery of the piping 2. Moreover, a pair of temperature sensor chips 6 is placed on the surface of the periphery of the piping 2 along the flowing direction of the mobile phase flowing through the piping 2. Of these, one of the temperature sensor chips 6a is placed on the upstream side of the heater chip 4, and the other temperature sensor chip 6b is placed on the downstream side of the heater chip 4.

With respect to the heater chip 4, for example, a chip diode ISS387 (product made by Toshiba Corporation) and a chip resistor RK73H1JT (product made by KOA Corporation) can be used. Moreover, with respect to the temperature sensor chips 6a and 6b, thermocouples and diodes that are formed in a chip type are used.

The paired temperature sensor chips 6a and 6b are respectively placed with an equal distance from the heater chip 4.

The heater chip 4 and the temperature sensor chips 6a and 6b are anchored onto the surface of the periphery of the piping 2 by using a thermal conductive adhesive, such as thermal conductive silicone sealant KE3467 (product made by Shin-Etsu Chemical Co., Ltd.).

As shown in FIG. 1B, in the state (dashed line) where no mobile phase is flowing through the piping 2, the temperature distribution is formed in a laterally symmetrical manner, with the position having the heater chip 4 anchored thereto being set to the apex of the temperature distribution, centered on the position of the apex. Therefore, in this state, the detected temperatures of the temperature sensor chips 6a and 6b are equal to each other.

A mobile phase is allowed to flow through the piping 2 (solid line), the apex of the temperature distribution is shifted toward the downstream side (right side in the figure), with the result that a difference occurs between the detected temperatures of the temperature sensor chips 6a and 6b. As the flow rate of the mobile phase flowing through the piping 2 becomes greater, the apex of the temperature distribution is further shifted toward the downstream side, and in the case where the apex of the temperature distribution is located between the temperature sensor chips 6a and 6b, as the apex of the temperature distribution is further shifted toward the downstream side, the difference between the detected temperatures of the temperature sensor chips 6a and 6b becomes greater. Therefore, since there is a correlation between the flow rate of the mobile phase and the detected temperature difference between the paired temperature sensor chips 6 made of the temperature sensor chips 6a and 6b, by preliminarily measuring this correlation so as to prepare as calibration line data, the flow rate of the mobile phase flowing through the piping 2 can be calculated from the detected temperature difference of the paired temperature sensor chips 6 based upon the calibration line.

The temperature sensor chips 6a and 6b are respectively connected to an operation unit, and the operation unit reads the measured temperatures of the temperature sensor chips 6a and 6b as signals, and in accordance with the temperature difference thereof, calculates the flow rate of the mobile phase flowing through the piping 2 based upon calibration line that is preliminarily found and stored. That is, the correlation between the detected temperature difference of the paired temperature sensor chips 6 and the flow rate of the fluid, preliminarily found, is stored in the operation unit as calibration lines, and the flow rate of a fluid flowing through the piping 2 can be automatically calculated based upon the difference in the detected temperatures of the paired temperature sensor chips 6. The operation unit is achieved by a CPU and a personal computer.

However, the above-mentioned correlation is held only when the apex of the temperature distribution is located between the paired temperature sensor chips 6. In the case where the flow rate of a fluid flowing through the piping 2 comes into a state in which the apex of the temperature distribution is shifted to the downstream side from the temperature sensor chip 6b and no longer exists between the paired temperature sensor chips 6, if the flow rate of the fluid flowing through the piping 2 increases to cause the temperature distribution to be further shifted toward the downstream side, the difference in the measured temperatures in the paired temperature sensor chips 6 decreases, with the result that the correlation between the flow rate and the measured temperature difference is no longer held; and consequently, it is not possible to calculate the flow rate by utilizing the correlation preliminarily measured based upon the measured temperature difference between the paired temperature sensor chips 6. In the present specification, the state in which the apex of the temperature distribution exceeds the corresponding paired temperature sensors to cause the correlation to be no longer satisfied is referred to as a "saturated state".

In order to avoid "the saturated state", it is necessary to widen an interval between the paired temperature sensor chips 6. By widening the interval between the paired temperature sensor chips 6, the present device can be applied to a high flow rate range with a larger amount of shift of the temperature distribution. However, in the case where a measuring process in a low flow rate range is carried out, with the interval between the paired temperature sensor chips 6 being set in a wider state, since the measured temperature difference between the paired temperature sensor chips 6 becomes smaller, the measuring sensitivity is lowered. In order to measure the flow rate of a fluid flowing through the piping 2 with high sensitivity, the paired temperature sensor chips 6 are preferably disposed with an appropriate interval relative to the flow rate range to be measured by the paired temperature sensor chips 6.

FIG. 2A is a cross-sectional view that shows one example of a thermal mass flow meter capable of measuring a wide flow-rate range from a low flow rate range to a high flow rate range, with high sensitivity, and FIGS. 2B and 2C are graphs that show temperature distributions of piping shown in FIG. 2A. In FIGS. 2B and 2C, the axis of ordinate indicates the temperature, and the axis of abscissas indicates the position of the piping 2 in the flowing direction. A curved line, represented by a dashed line, indicates a temperature distribution of the surface of the piping 2, given by the heater chip 4 in a state with no fluid flowing through the piping, and a curved line, represented by a solid line, indicates a temperature distribution of the surface of the piping 2, given by the heater 4 in a state with a fluid flowing through the piping 2.

In FIG. 2A, the heater chip 4 is anchored onto the surface of the periphery of the piping 2 that constitutes a high-pressure liquid chromatograph. In this embodiment, the mobile phase is allowed to flow through the pipe 2 from the left side to the right side in the figure. The paired temperature sensor chips 6, made of the two temperature sensor chips 6a and 6b that are placed as a pair located on the upstream side and the downstream side of the heater chip 4 along the flowing direction of the mobile phase flowing through the piping 2, are placed closely to the heater chip 4. The temperature sensor chip 6a is placed on the upstream side of the heater chip 4, and the temperature sensor chip 6b is placed on the downstream side of the heater chip 4.

A temperature sensor chip 8a is placed on the further upstream side of the temperature sensor chip 6a, and a temperature sensor chip 8b is placed on the further downstream side of the temperature sensor chip 6b. The temperature sensor chips 8a and 8b constitute a pair of temperature sensor chips 8.

A temperature sensor chip 10a is placed on the further upstream side of the temperature sensor chip 8a, and a temperature sensor chip 10b is placed on the further downstream side of the temperature sensor chip 8b. The temperature sensor chips 10a and 10b constitute a pair of temperature sensor chips 10.

In this embodiment, each of the temperature sensor chips 6a, 6b, 8a, 8b, 10a and 10b has a structure in which a diode is formed in a chip state.

The respective two temperature sensor chips 6a, 6b, 8a, 8b, and 10a, 10b, formed into the respective pairs, are placed with an equal distance from the heater chip 4 respectively.

The heater chip 4 and the temperature sensor chips 6a, 6b, 8a, 8b, 10a and 10b are anchored onto the surface of the periphery of the piping 2 by using a thermal conductive bonding agent, such as thermal conductive silicone sealant KE3467 (product made by Shin-Etsu Chemical Co., Ltd.).

The temperature sensor chips 6a, 6b, 8a, 8b, 10a and 10b are respectively connected to an operation unit constituted by a CPU or a personal computer. The operation unit reads the detected temperatures of the temperature sensor chips 6a, 6b, 8a, 8b, 10a and 10b as signals, and in accordance with the measured temperature difference of each of pairs of temperature sensor chips 6a and 6b, 8a and 8b, and 10a and 10b, serving as paired temperature sensor chips, calculates the flow rate of a mobile phase flowing through the piping 2. That is, the correlation between the flow rate of the mobile phase flowing through the piping 2 and the measured temperature difference between each of the pairs of temperature sensor chips 6, 8 and 10 that have been preliminarily measured is stored in the operation unit as a calibration line, and based upon the calibration line, the flow rate can be calculated from the measured temperature difference between each of the pairs of temperature sensor chips 6, 8 and 10.

The following description will discuss FIGS. 2B and 2C. Here, it is supposed that the measured temperature difference between the paired temperature sensor chips 6 is ΔT1, that the measured temperature difference between the paired temperature sensor chips 8 is ΔT2, and that the measured temperature difference between the paired temperature sensor chips 10 is ΔT3.

In the case where the flow rate of a mobile phase flowing through the piping 2 is in a low flow rate range, for example, in the order of nL/min, the shift of the temperature distribution of the surface of the pipe 2 toward the downstream side is small, and as shown in FIG. 2B, the apex of the temperature distribution is located between the paired temperature sensor chips 6. In this case, since each of the apexes of the temperature distributions is located between each pair of the paired temperature sensor chips 6, 8, and 10, the flow rate of a fluid flowing through the piping 2 can be found from the measured temperature differences ΔT1, ΔT2 and ΔT3 in the respective paired temperature sensors, based upon each of the correlations. In the case where the amount of shift of the temperature distribution is small, since the paired temperature sensor chips 6, placed closely to the heater chip 4, are allowed to measure the temperature at a position having an abrupt inclination in the temperature distribution curve, they can detect a comparatively large value as a measured temperature difference ΔT1 even when the flow rate is small. In contrast, the paired sensor chips 8 and 10 are made to measure the temperature at a position having a more moderate inclination than that of the paired temperature sensor chips 6 in the temperature distribution curve, with the result that only the values smaller than ΔT1 can be obtained as the measured temperature differences ΔT2 and ΔT3. Therefore, in the case where the flow rate of a mobile phase flowing through the piping 2 is in a low flow rate range, the paired temperature sensor chips 6 having the narrowest placement interval can be used to carry out the measurements so that it is possible to carry out the flow rate measurements with high sensitivity. In general, among the paired temperature sensor chips 6, 8 and 10, the operation unit uses such paired temperature sensors in which the temperature sensor on the downstream side is located on the downstream side from the apex position of the temperature distribution of a fluid flowing through the piping, and positioned closest to the apex position, to find the flow rate.

As shown in FIG. 2C, in the case where the flow rate increases beyond the rate as shown in FIG. 2B so that the temperature distribution is further shifted toward the downstream side, with the apex of the temperature distribution being no longer located between each pair of the paired temperature sensor chips 6 and 8, since "the saturated state" has been reached with respect to the paired temperature sensor chips 6 and 8, the flow rate cannot be calculated from the measured temperature difference of the paired temperature sensor chips 6 and 8 based upon the calibration line. In this case, since the apex of the temperature distribution is still located between the paired temperature sensor chips 10, the flow rate can be calculated from the measured temperature difference of the paired temperature sensor chips 10 based upon the calibration line.

Moreover, although not shown in the figure, in the case where the apex of the temperature distribution is not located between the paired temperature sensor chips 6, but located between the paired temperature sensor chips 8 and 10, the flow rate can be calculated from either of the measured temperature differences of the paired temperature sensor chips 8 and 10. However, since the paired temperature sensor chips 8 make it possible to detect a greater measured temperature difference, and consequently to carry out the flow rate measurements with high sensitivity, the paired temperature sensor chips 8 are more preferably used to carry out the measurements.

In this embodiment, three pairs of the paired sensor chips 6, 8 and 10 are placed on the surface of the periphery of the piping 2. However, the present invention is not intended to be limited to this structure, and two pairs or four pairs or more of paired temperature sensors may be provided.

As shown in this embodiment, by providing a plurality of pairs of paired sensor chips between a position close to the heater chip 4 and a position apart from the heater chip 4, flow rate measurements can be carried out by using any pair of temperature sensor chips that are capable of measuring in a wide flow rate range from a low flow rate range to a high flow rate range. In such a thermal mass flow meter, among the paired temperature sensor chips that have not been reached the saturated state within the flow rate range to be measured, the paired temperature sensor chips having the pair of temperature sensor chips disposed with the narrowest interval is preferably used to carry out the flow rate measurements. With this arrangement, the measured temperature difference between the paired temperature sensor chips can be detected as a great value, and the flow rate measurements are consequently carried out with high sensitivity.

Referring to, for example, a flowchart shown in FIG. 3, the following description will discuss one example of a determination method for the apex position of the temperature distribution in the embodiments described by reference to FIGS. 2A, 2B and 2C. In FIG. 3, "i" represents the number of samplings of temperature data obtained by the thermal mass flow meter of FIG. 2, and the sampling is carried out for every constant interval. When the number of samplings is "i", the detected temperature differences of the respective paired sensor chips 6, 8 and 10 are represented by ΔT1[i], ΔT2[i] and ΔT3[i]. Moreover, in the state where no fluid is flowing, it is supposed that i=0, ΔT1[0]=A, ΔT2[0]=B and ΔT3[0]=C, and that A, B and C are constants. It is supposed that A, B and C have been preliminarily stored in the operation unit.

Here, [Condition 1] of step S3, [Condition 2] of step S5 and [Condition 3] of step S7 in FIG. 3 are shown as follows:

$$\Delta T1[i-1]<\Delta T1[i],$$

$$\Delta T2[i-1]<\Delta T2[i] \text{ and}$$

$$\Delta T3[i-1]<\Delta T3[i],$$

or $$\Delta T1[i-1]>\Delta T1[i],$$

$$\Delta T2[i-1]>\Delta T2[i] \text{ and}$$

$$\Delta T3[i-1]>\Delta T3[i] \qquad \text{[Condition 1]}$$

$$\Delta T1[i-1]>\Delta T1[i],$$

$$\Delta T2[i-1]<\Delta T2[i] \text{ and}$$

$$\Delta T3[i-1]<\Delta T3[i],$$

or $$\Delta T1[i-1]<\Delta T1[i],$$

$$\Delta T2[i-1]>\Delta T2[i] \text{ and}$$

$\Delta T3[i-1] > \Delta T3[i]$     [Condition 2]

$\Delta T1[i-1] > \Delta T1[i]$, $\Delta T2[i-1] > \Delta T2[i]$ and $\Delta T3[i-1] < \Delta T3[i]$, or $\Delta T1[i-1] < \Delta T1[i]$, $\Delta T2[i-1] < \Delta T2[i]$ and $\Delta T3[i-1] > \Delta T3[i]$     [Condition 3]

Upon starting measuring operations (initial state: i=0), $\Delta T1[0]$=A, $\Delta T2[0]$=B and $\Delta T3[0]$=C. After setting i=1 (step S1), the detected temperature differences $\Delta T1[i]$, $\Delta T2[i]$ and $\Delta T3[i]$ of the respective paired temperature sensor chips are incorporated (step S2). It is determined whether or not $\Delta T1[i]$, $\Delta T2[i]$ and $\Delta T3[i]$, thus being incorporated, fall under [Condition 1] (step S3). When these fall under [Condition 1], it is determined that the apex of the temperature distribution is located between the heater chip 4 and the temperature sensor chip 6a (step S4), and after setting i=i+1, the procedure returns to step S2. When these do not fall under [Condition 1], it is determined whether or not these fall under [Condition 2] (step S5). When these fall under [Condition 2], it is determined that the apex of the temperature distribution is located between the temperature sensor chip 6a and the temperature sensor chip 8a (step S6), and after setting i=i+1, the procedure returns to step S2. When these do not fall under [Condition 2], it is determined whether or not these fall under [Condition 3] (step S7). When these fall under [Condition 3], it is determined that the apex of the temperature distribution is located between the temperature sensor chip 8a and the temperature sensor chip 10a (step S8), and after setting i=i+1, the procedure returns to step S2. When these do not fall under [Condition 3], it is determined that the apex of the temperature distribution is located further on the downstream side (step S9) from the temperature sensor chip 10a (step S9), and after setting i=i+1, the procedure returns to step S2.

Based upon the apex positions of the temperature distributions determined by the above-mentioned procedure, it is possible to select the paired temperature sensor chips that are most suitable for the flow rate measuring operation under the condition. That is, as shown in step S4 of FIG. 3, upon determination that the apex of the temperature distribution is located between the heater chip 4 and the temperature sensor chip 6a, the paired temperature sensor chips 6 are most suitable for the measuring operation; as shown in step S6, upon determination that the apex of the temperature distribution is located between the temperature sensor chip 6a and the temperature sensor chip 8a, the paired temperature sensor chips 8 are most suitable for the measuring operation; and upon determination that the apex of the temperature distribution is located between the temperature sensor chip 8a and the temperature sensor chip 10a, the paired temperature sensor chips 10 are most suitable for the measuring operation.

In the thermal mass flow meter shown in FIGS. 1A and 2A, in the case where the piping 2 is a capillary having such a small outer diameter that it is difficult to directly anchor the heater chip 4 and the temperature sensor chips 6, 8 and 10 onto the piping 2, by utilizing a substrate, the attaching processes of the heater chip 4 and the temperature sensor chips 6, 8 and 10 can be easily carried out. In addition to a resin substrate such as a silicone substrate, for example, a substrate forming a wiring pattern thereon, such as a printed circuit board, may be utilized as a substrate in this case. FIG. 4 shows drawings that show forming processes to be used for describing one embodiment of a thermal mass flow meter utilizing a printed circuit board. FIGS. 4(1a), (2a), (3a) and (4a) are plan views showing the respective processing steps, and FIGS. 4(1b), (2b), (3b) and (4b) are expanded cross-sectional views taken at X-X positions of FIGS. 4(1a), (2a), (3a) and (4a).

Reference numeral 12 represents a printed circuit board in which a plurality of wiring patterns 14 are formed on the surface of, for example, a glass epoxy substrate, a polyimide substrate, or the like. As shown in FIGS. 4(1a) and 4(1b), a groove 16 larger than the outer diameter of the piping 2 is formed on the surface side of the printed circuit board 12. The groove 16 is designed in its formation position so that the wiring pattern 14 is disposed symmetrically in a perpendicular direction relative to the groove 16 outside thereof, with the groove 16 being interposed therebetween.

As shown in FIGS. 4(2a) and 4(2b), the piping 2 is embedded into the groove 16, and anchored to the printed circuit board 12 by using a heat-resistant adhesive 18, such as, for example, a heat insulating silicone sealant SE-9120 (product made by Dow Corning Toray Silicone Co., Ltd.). The surface of the periphery of the piping 2 is exposed to the surface side of the printed circuit board 12.

As shown in FIGS. 4(3a) and 4(3b), the heater chip 4 and the paired temperature sensor chips 6 are anchored onto the surface of the periphery of the piping 2 exposed to the surface side of the printed circuit board 12, by using a thermal conductive adhesive 20. In this embodiment, a chip-type temperature sensor chip, such as, for example, a chip-type diode in which a diode is formed inside the chip, is used as temperature sensor chips 6a and 6b constituting the paired temperature sensor chips 6. Such a temperature sensor chip is provided with a lead terminal externally formed thereon, and an inner sensor unit is connected to the lead terminal. The lead terminals of the temperature sensor chips 6a and 6b are electrically connected to the wiring pattern 14 by using, for example, solder connection.

As shown in FIGS. 4(4a) and 4(4b), the groove 16 portion including the surface of the periphery of the piping 2 exposed to the surface side of the printed circuit board 12 is covered with a heat-insulating member 22, made from, for example, Toray Pef (registered trade mark: product of Toray Pef products, Inc.). Thus, the temperature sensor chips 6a and 6b are blocked from contacting with the outside air so that the temperature measuring operations can be carried out without being influenced by the outside air.

Although not shown in the Figures, the wiring pattern 14 to which the temperature sensor chips 6a and 6b are connected is connected to the operation unit that reads signals from the respective temperature sensor chips 6a and 6b, and calculates the flow rate based upon the measured temperature difference of the paired temperature sensor chips 6.

In this embodiment, a pair of temperature sensor chips 6 is provided; however, as shown in FIG. 5, three pairs of paired temperature sensor chips 6, 8 and 10, as shown in FIG. 2A, may be provided. Moreover, not limited to the structure shown in FIGS. 4 and 5, the thermal mass flow meter of the present invention may be provided with two pairs or four pairs or more of paired temperature sensors. Here, in FIG. 5, the heat insulating member 22 is drawn by a chain line, and the heater chip 4, the temperature sensor chips 6a, 6b, 8a, 8b, 10a and 10b can be seen on the surface of the printed circuit board 12; however, actually, the heater chip 4, the temperature sensor chips 6a, 6b, 8a, 8b, 10a and 10b are covered with the heat insulating member 22.

In this manner, by attaching the heater chip 4 and the temperature sensor chips 6a, 6b, 8a, 8b, 10a and 10b to piping 2, with the piping 2 being secured to the substrate, it becomes possible to easily attach the heater chip 4 and the temperature sensor chips 6a, 6b, 8a, 8b, 10a and 10b thereto, in particular, in the case where the piping 2 is a capillary or the like having a small outer diameter. Moreover, by using a wiring board such as a printed circuit board 12 as the substrate for securing the piping 2, it becomes possible to easily draw out the terminals of elements such as the heater chip 4 and the temperature sensor chips 6a, 6b, 8a, 8b, 10a and 10b.

Here, the thermal mass flow meter, shown in FIGS. 4 and 5, uses the printed circuit board 12 as the substrate used for securing the piping 2; however, the present invention is not limited to this structure, and a substrate having no wiring pattern formed thereon may be used.

Moreover, for example, those structures as shown in FIG. 6A and FIG. 6B may be used as other structures in which the substrate is utilized. That is, the thermal mass flow meter, shown in FIG. 6A and FIG. 6B, uses a printed circuit board 24 forming a wiring pattern 26 thereon as the substrate, and the printed circuit board 24 is provided with a groove 25, formed thereon, to which the main body portions of the heater chip 4 and the temperature sensor chips 6a, 6b, 8a, 8b, 10a and 10b are fitted, with their upper faces facing down. The wiring pattern 26 is drawn outward from the groove 25, and the width dimension of the groove 25 is formed so that gaps are formed between the main body portions thereof and the printed circuit board 24, with the heater chip 4 and the temperature sensor chips 6a, 6b, 8a, 8b, 10a and 10b being fitted thereto. The terminals of the heater chip 4 and the temperature sensor chips 6a, 6b, 8a, 8b, 10a and 10b fitted to the groove 25 are kept in contact with the wiring patterns 26 on the sides of the groove 25, and electrically connected thereto by using, for example, solder connection. The piping 2 is anchored on the heater chip 4 and the temperature sensor chips 6a, 6b, 8a, 8b, 10a and 10b, with a thermal conductive adhesive 28, such as, for example, thermal conductive silicone sealant KE3467 (product made by Shin-Etsu Chemical Co., Ltd.), being interposed therebetween.

Additionally, in the thermal mass flow meter shown in FIGS. 6A and 6B, three pairs of the paired temperature sensor chips 6, 8 and 10 are secured to the printed circuit board 24; however, one pair, two pairs or four pairs or more of paired temperature sensors may be anchored thereon.

DESCRIPTION OF THE REFERENCE NUMERALS

Figure 1A:
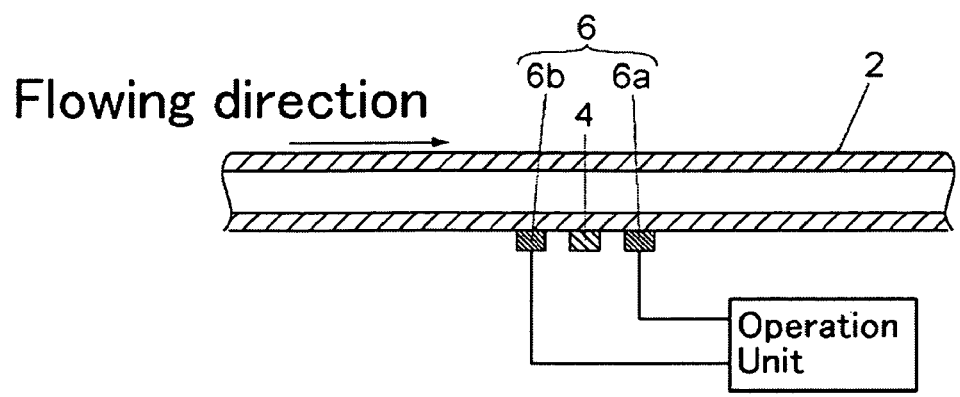
FIG. 1A is a cross-sectional view that shows one embodiment of a thermal mass flow meter used for measuring the flow rate of a fluid flowing through piping.
Figure 1B:
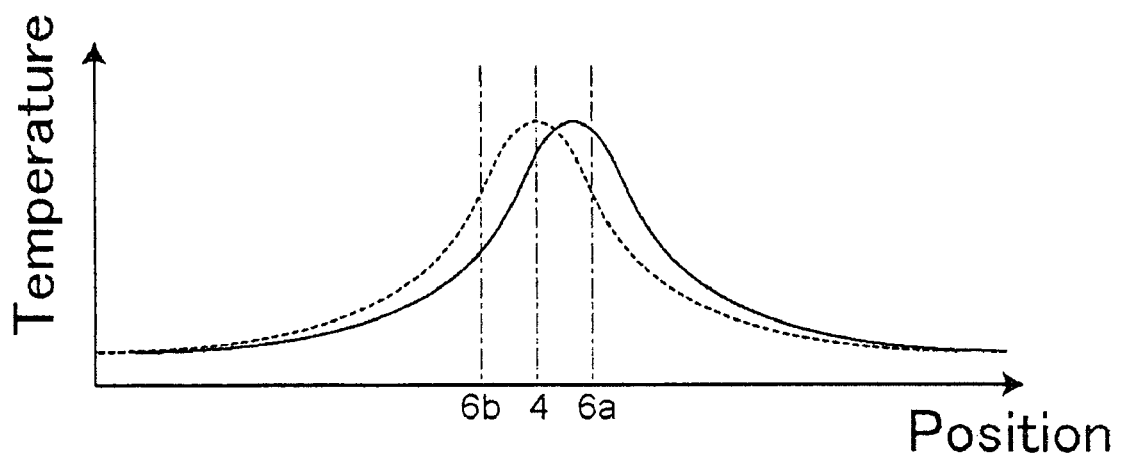
FIG. 1B is a graph that shows a temperature distribution of the piping.
Figure 2A:
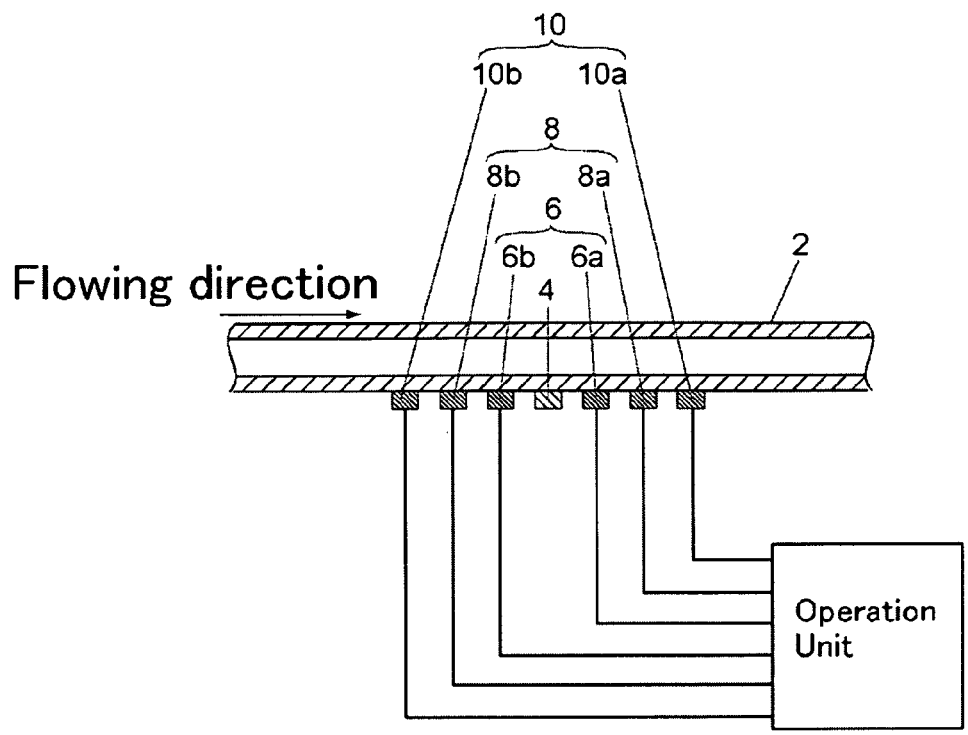
FIG. 2A is a cross-sectional view that shows one embodiment of a thermal mass flow meter that can measure the flow rate over a wide range from a low flow rate range to a high flow rate range with high sensitivity.
Figure 2B:
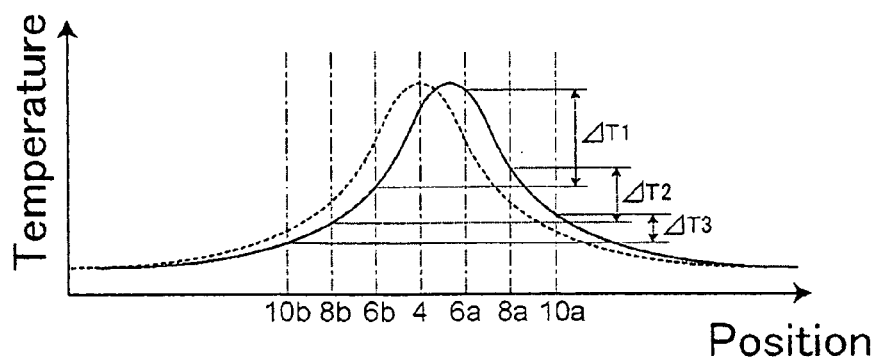
FIG. 2B is a graph that shows a temperature distribution during a low flow rate operation of the piping of FIG. 2A.
Figure 2C:
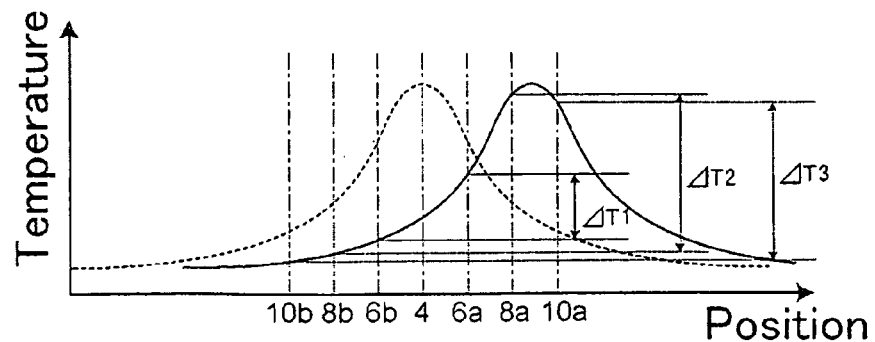
FIG. 2C is a graph that shows a temperature distribution during a high flow rate operation of the piping of FIG. 2A.
Figure 3:
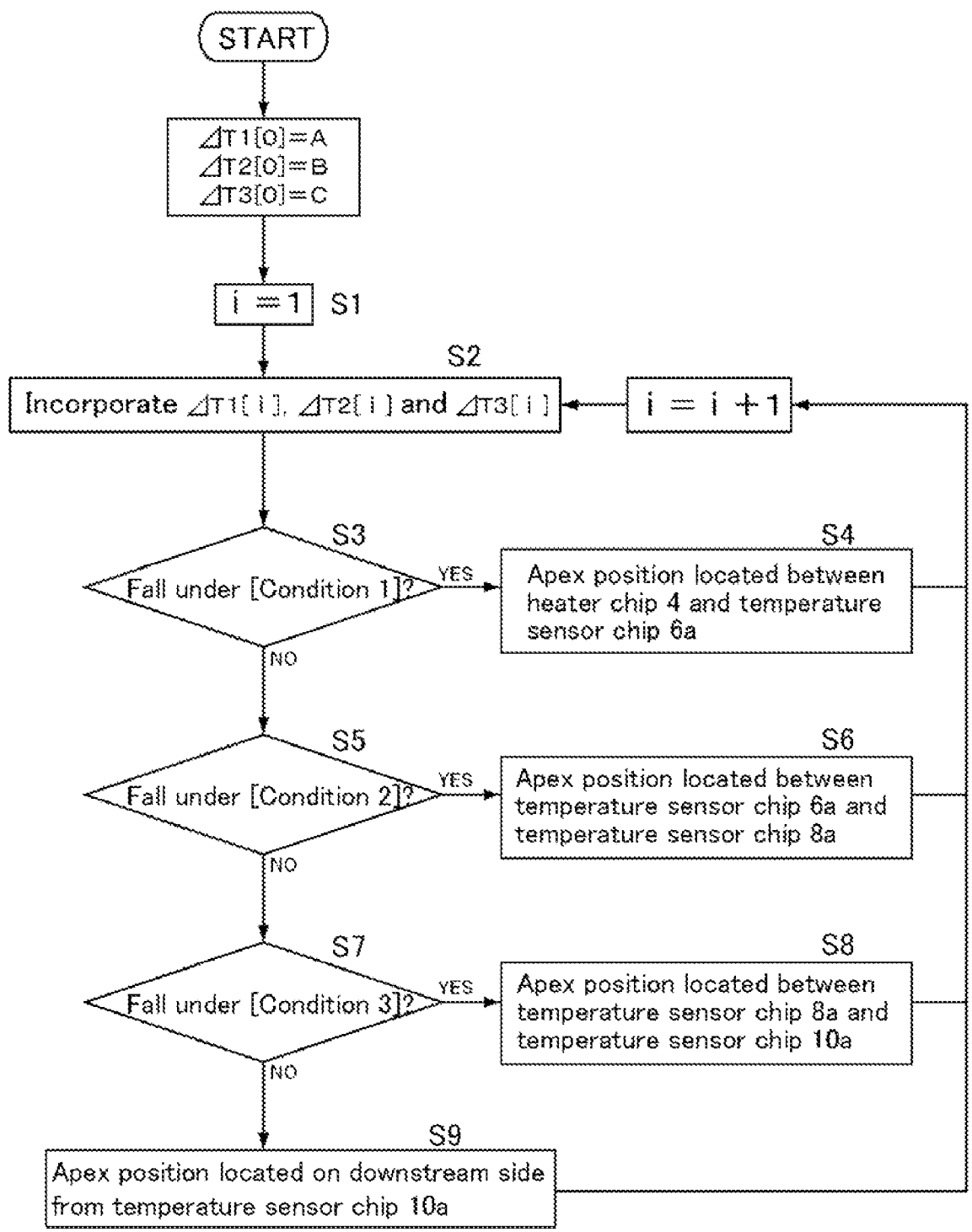
FIG. 3 is a flow chart that shows a determining method for the apex position of the temperature distribution.
Figure 4:
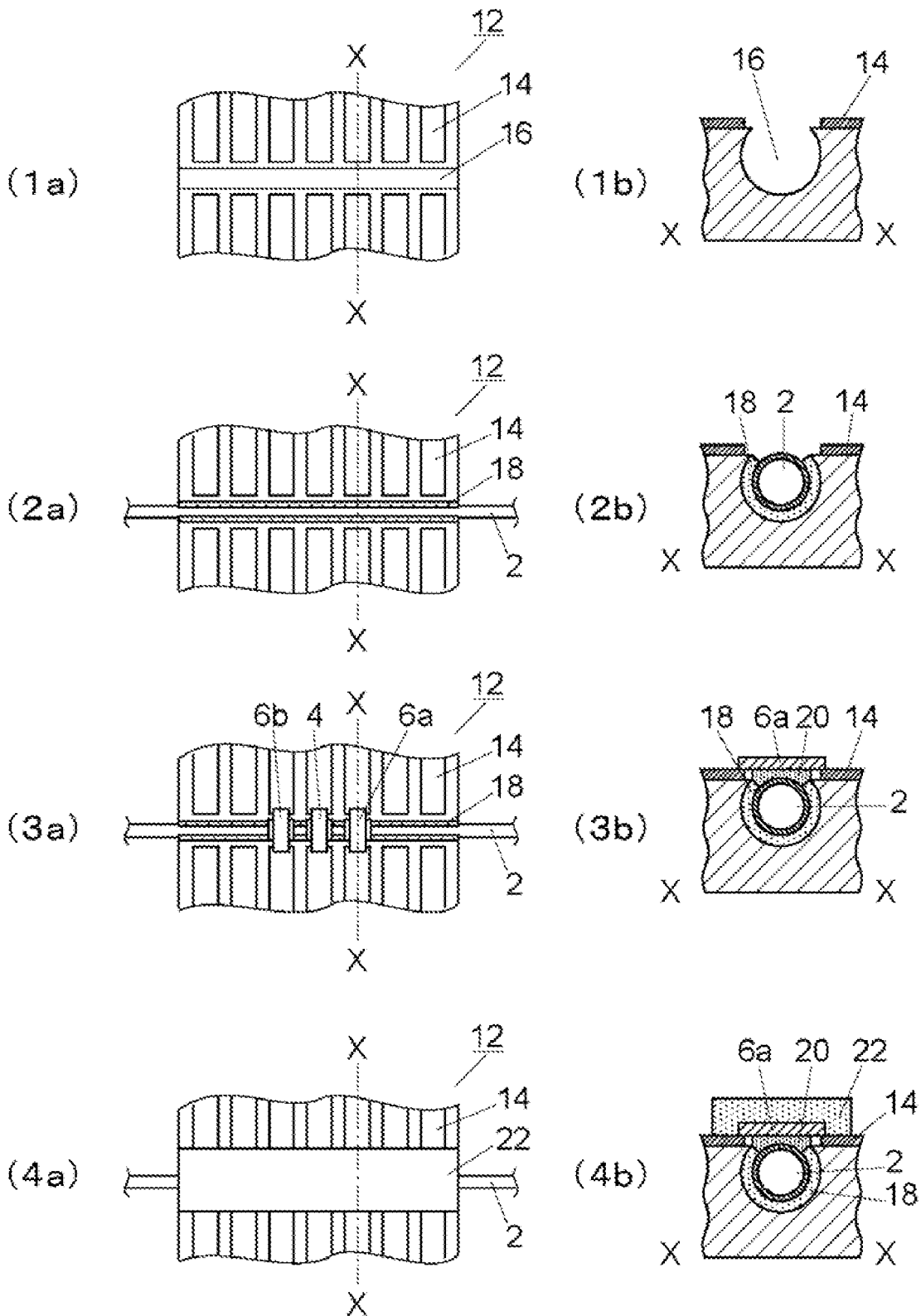
FIG. 4 shows drawings that show forming processes for manufacturing one embodiment of a thermal mass flow meter utilizing a printed circuit board, includes FIGS. 4(1a), (2a), (3a) and (4a) corresponding to plan views showing the respective processing steps, and FIGS. 4(1b), (2b), (3b) and (4b) that are expanded cross-sectional views taken at X-X positions of FIGS. 4(1a), (2a), (3a) and (4a).
Figure 5:
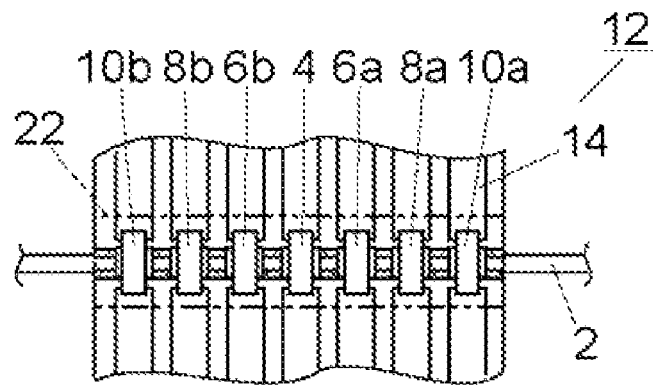
FIG. 5 is a plan view that shows still another embodiment of a thermal mass flow meter utilizing a printed circuit board.
Figure 6A:
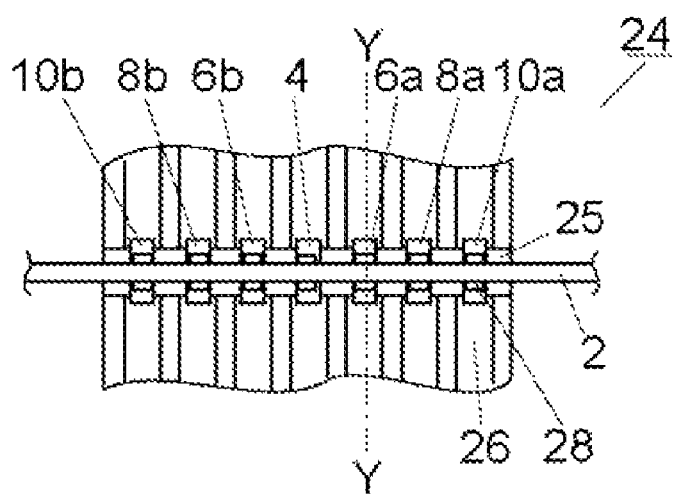
FIG. 6A is a plan view that shows the other embodiment of a thermal mass flow meter utilizing a printed circuit board.
Figure 6B:
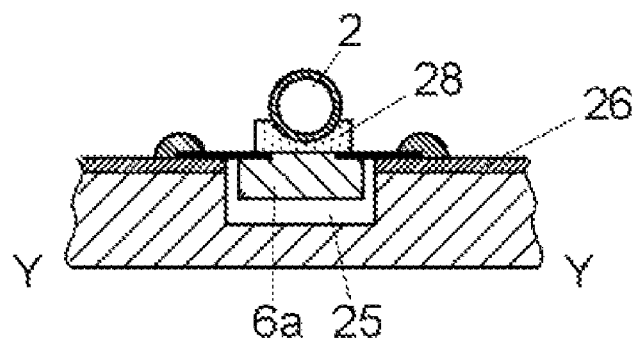
FIG. 6B is an enlarged cross-sectional view at Y-Y position of FIG. 6A.
Figure 7A:
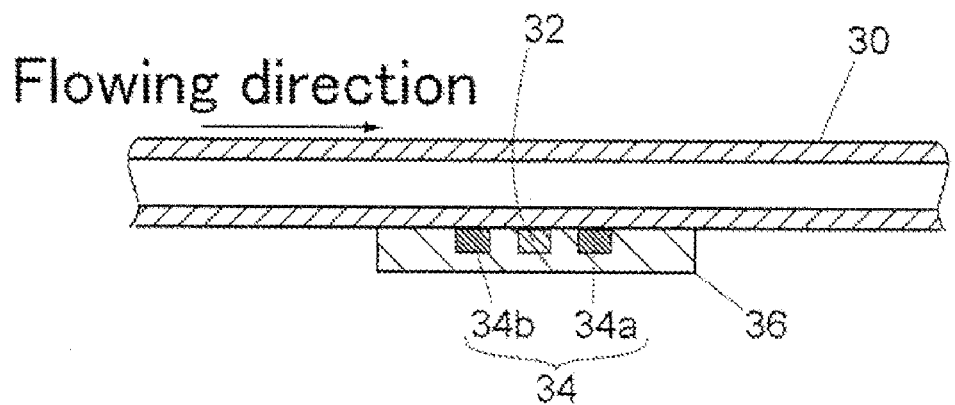
FIG. 7A is a cross-sectional view that shows one example of a conventional thermal mass flow meter.
Figure 7B:
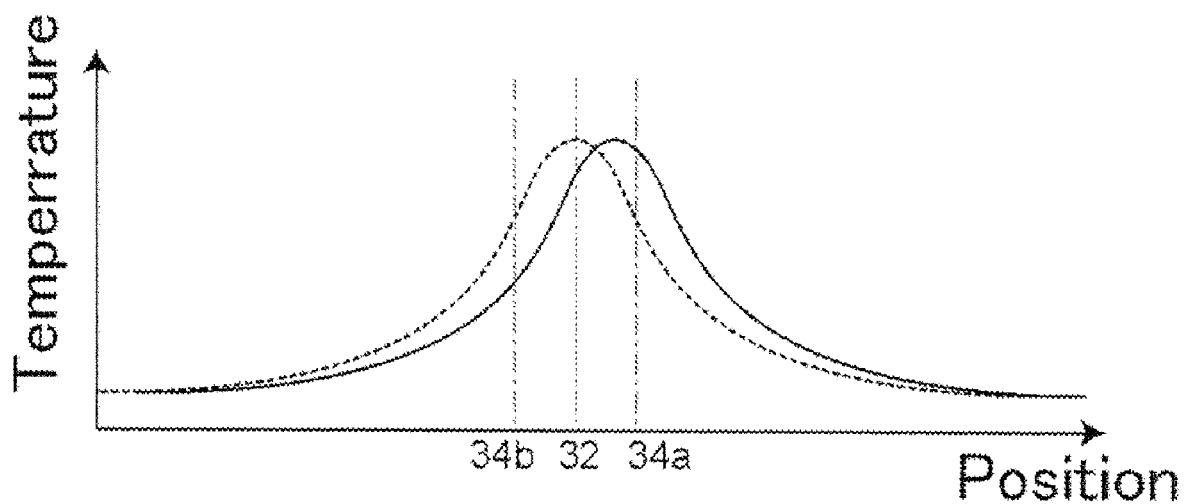
FIG. 7B is a graph that shows a temperature distribution of the surface of piping shown in FIG. 7A.

2 Piping
4 Heater chip
6, 8, 10 Paired temperature sensor chips
6a, 6b, 8a, 8b, 10a, 10b Temperature sensor chip
12, 24 Printed circuit board
14, 26 Wiring pattern
16 Groove
18 Heat-insulating adhesive
20, 28 Thermal conductive adhesive
22 Heat-insulating member

What is claimed is:

1. A thermal mass flow meter comprising:
   a heat generating element of a chip type for heating a fluid inside piping, the heat generating element being secured onto a surface of a periphery of the piping through which the fluid is flowing;
   paired temperature sensors of a chip type formed as members separated from the heat generating element, the paired temperature sensors being secured to positions on the upstream side and the downstream side of the heat generating element on the surface of the piping, with an equal distance apart therefrom, along the flowing direction of the fluid inside the piping; and
   an operation unit for finding the flow rate of the fluid flowing through the piping from the temperature difference of the paired temperature sensors;
   wherein the heat generating element of a chip type consists of a chip diode or a chip resistor.

2. The thermal mass flow meter according to claim 1, wherein
   the paired temperature sensors include two pairs or more being placed at positions having different distances from the heat generating element, and
   the operation unit finds the flow rate by using temperature measuring signals from any of the pairs of the temperature sensors in response to the scale of the flow rate.

3. The thermal mass flow meter according to claim 2, wherein
   the operation unit finds the flow rate by using the pair of the temperature sensors in which the temperature sensor on the downstream side is located on the downstream side from the apex position of the temperature distribution of the fluid flowing through the piping and is located closest to the apex position, among the paired temperature sensors.

4. The thermal mass flow meter according to claim 1, wherein
   the heat generating element and temperature sensors are secured to the piping through a bonding process with a thermal conductive adhesive.

5. The thermal mass flow meter according to claim 1, wherein
the piping is embedded in a groove on a substrate so that a part of the surface of the periphery of the piping is exposed, and
the heat generating element and temperature sensors are secured to the exposed surface.

6. The thermal mass flow meter according to claim 5, wherein
the substrate is a printed circuit board on which conductor traces are formed, and
the heat generating element and the temperature sensors are electrically connected to the conductor traces.

7. The thermal mass flow meter according to claim 1, wherein
the heat generating element and temperature sensors are supported on a substrate and secured thereto, and
the piping is anchored on the heat generating element and temperature sensors.

8. The thermal mass flow meter according to claim 7, wherein
the substrate is a printed circuit board on which conductor traces are formed, and
the heat generating element and the temperature sensors are electrically connected to the conductor traces.

9. The thermal mass flow meter according to claim 1, wherein
the piping is piping through which a mobile phase is allowed to flow in high-pressure liquid chromatograph.

* * * * *